United States Patent
Newton et al.

(10) Patent No.: US 6,716,887 B2
(45) Date of Patent: Apr. 6, 2004

(54) FISCHER-TROPSCH PROCESS

(75) Inventors: David Newton, Farnham (GB); Barry Nay, Woking (GB)

(73) Assignee: BP Exploration Operating Company Limited, London (GB)

(*) Notice: Subject to any disclaimer, the term of this patent is extended or adjusted under 35 U.S.C. 154(b) by 0 days.

(21) Appl. No.: 10/297,253

(22) PCT Filed: May 23, 2001

(86) PCT No.: PCT/GB01/03329
§ 371 (c)(1),
(2), (4) Date: May 8, 2003

(87) PCT Pub. No.: WO01/94499
PCT Pub. Date: Dec. 13, 2001

(65) Prior Publication Data
US 2003/0195264 A1 Oct. 16, 2003

(30) Foreign Application Priority Data
Jun. 6, 2000 (GB) ............................................. 0013793

(51) Int. Cl.[7] ............................................... C07C 27/00
(52) U.S. Cl. ...................... 518/715; 518/700; 518/705
(58) Field of Search ................................ 518/700, 705, 518/715

(56) References Cited

U.S. PATENT DOCUMENTS

| 2,646,442 A | 7/1953 | Kendall |
| 5,348,982 A | 9/1994 | Herbolzheimer et al. |

*Primary Examiner*—J. Parsa
(74) *Attorney, Agent, or Firm*—Nixon & Vanderhye

(57) ABSTRACT

A process for the production of liquid hydrocarbon products by passing, at elevated temperature and pressure, synthesis gas and a fluidizing liquid through a fluidized catalytic bed within a reaction zone, characterized in that the fluidized catalytic bed is an aggregative fluidized catalytic bed comprising a particulate Fischer-Tropsch catalyst having a density of greater than 4,000 kg/m$^3$.

24 Claims, 1 Drawing Sheet

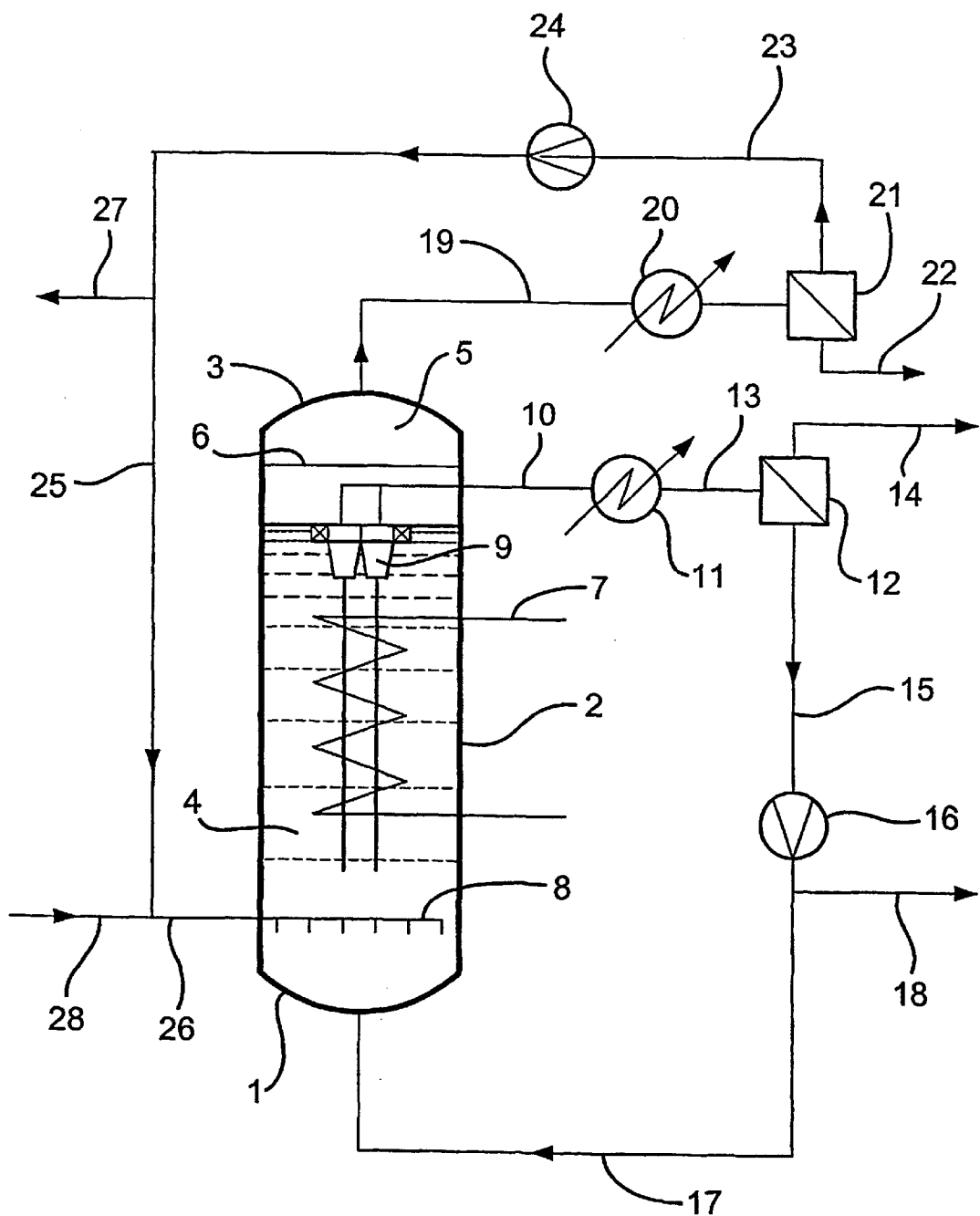

FISCHER-TROPSCH PROCESS

This application is a 371 of PCT/GB01/02329 filed May 23, 2001

The present invention relates to a process for the production of liquid hydrocarbons from a gaseous mixture comprising carbon monoxide and hydrogen (synthesis gas), in the presence of a Fischer-Tropsch catalyst. In particular, the present invention relates to the production of liquid hydrocarbons by contacting synthesis gas with a Fischer-Tropsch catalyst in an aggregative fluidised bed.

The production of hydrocarbons by contacting synthesis gas with a Fischer-Tropsch catalyst, typically a cobalt or iron catalyst, which may be either supported or unsupported, has been known for a considerable number of years. Fischer-Tropsch processes have been operated commercially, for example, by Sasol Technology (Pty) Ltd in South Africa. Much of the early work on Fischer-Tropsch hydrocarbon synthesis was accomplished using fixed bed catalysts but in recent times attention has shifted to the use of liquid phase catalytic reactions largely because of the relative ease of removing the exothermic heat of reaction in such systems. Liquid phase Fischer-Tropsch processes typically employ a three-phase (liquid/gas/solid) slurry medium. In particular, use of fluidised beds in Fischer-Tropsch processes is known.

In a fluidised bed, solid particles are transformed into a fluid-like state by the upward passage of a gas or liquid (fluidising fluid). When the velocity of the fluidising fluid reaches a critical velocity the drag force on the solid particles equals the buoyant weight of the bed. The bed is then supported by the fluidising fluid and possesses fluid-like properties such as flowing easily and maintaining a horizontal level when the bed is tilted. In addition, low density objects may be floated on the surface of the bed. This state is known as "fluidisation", and the critical superficial fluid velocity at which this occurs is termed the "minimum fluidisation velocity". When the fluidising fluid is a liquid (i.e. a liquid-solid system), an increase in the rate of flow of the liquid above the minimum fluidisation conditions, generally results in a progressive expansion of the bed, which gives rise to what is termed "particulate" or "homogeneous fluidisation". For large diameter fluidised beds, the expansion of a particulate fluidised bed can be approximated by the relationship:

$$U = U_t \epsilon^n$$

where U is the superficial liquid velocity, $U_t$ is the terminal fall velocity of the solid particles, $\epsilon$ is the voidage of the solid particles, and n is the Richardson and Zaki exponent which is dependent upon the terminal Reynolds number, $Re_t$ and ranges from n=2.4 ($Re_t$>500) to n=4.65 ($Re_t$<0.2). The exponent n is also a function of the particle-to-bed diameter ratio, d/D, as described by Yates in "Fundamentals of Fluidised-Bed Chemical Processes", Butterworths 1983, pages 14–15. This relationship can generally be ignored for small particles in large diameter beds.

Fischer-Tropsch processes which employ particulate fluidised beds in slurry bubble column reactors are described in, for example, U.S. Pat. Nos. 5,348,982; 5,157,054; 5,252,613; 5,866,621; 5,811,468; and 5,382,748. Slurry bubble column reactors operate by suspending catalytic particles in a liquid and feeding gas phase reactants into the bottom of the reactor through a gas distributor which produces small gas bubbles. As the gas bubbles rise through the reactor, the reactants are absorbed into the liquid and diffuse to the catalyst where, depending on the catalytic system, they can be converted to both liquid and gaseous products. If gaseous products are formed, they enter the gas bubbles and are collected at the top of the reactor. Liquid products are recovered by passing the slurry through a filter which separates the liquid from the catalytic solids. In slurry bubble columns mixing is effected by the action of the rising gas bubbles.

In U.S. Pat. No. 5,776,988, a Fischer-Tropsch process is operated by passing liquid and gas through the reactor in an ascending flow so as to expand a particulate fluidised catalytic bed by at least 10% and up to 50% in relation to the height of the bed at rest and to place the catalyst in random movement in the liquid. By controlling the size and density of the catalytic particles, and the velocities of the gases and of the liquids, while taking into account the viscosity of the liquid and the operating conditions, the catalytic bed expands to a controlled height. The size of the catalyst is typically of mean equivalent diameter of between 100 and 5000 $\mu$m. A commercial scale plant operated according to the process of U.S. Pat. No. 5,776,988 would require a catalytic bed of several meters in diameter and several meters deep.

However, a limitation to particulate fluidisation, particularly when applied to Fischer-Tropsch processes, is the marked relationship between the liquid fluidising velocity and the catalyst size and density. In order to avoid expansion of the bed out of the reaction vessel, a superficial liquid velocity must be employed below that of the terminal fall velocity, $U_t$, of the solid particles. To increase the "window" of operability of a commercial process, a larger catalyst particle size can be used which increases the terminal fall velocity, $U_t$, and hence allows a higher superficial liquid velocity to be employed. Generally, in order to prevent segregation of the catalyst particles, a very narrow particle size distribution is employed (often referred to as monosized catalyst particles).

A different type of fluidisation behaviour is observed when the solid particles have a density which is considerably higher than that of the fluidising liquid. This type of fluidisation is called "aggregative" or "bubbling" fluidisation. The fundamental reasons for the transition from particulate to aggregative fluidisation is not well understood but, without wishing to be bound by any theory, an important factor is the density ratio, $\rho_s/\rho_f$, where $\rho_s$ is the density of the solid particles and $\rho_f$ is the density of the fluidising fluid. If the density ratio is high, aggregative behaviour is obtained; if the ratio is low, particulate fluidisation is observed. For particles having an average diameter in the range of 50 to 1000 $\mu$m, fluidised with liquids having a density in the range of 700 to 1000 kg/m$^3$, the transition from particulate to aggregative fluidisation occurs for solid particles having a density of greater than approximately 4000 kg/m$^3$.

Expansion of an aggregative fluidised bed does not follow the relationship:

$$U = U_t \epsilon^n.$$

Instead, aggregative fluidised beds are characterised by the formation of particle free regions of fluidising liquid above the minimum fluidisation conditions. These particle free regions of fluidising liquid may be regarded as liquid "bubbles" or liquid "voids".

Surprisingly, it has now been found that a Fischer-Tropsch process can be successfully operated using an aggregative fluidised catalytic bed.

The present invention relates to a process for the production of liquid hydrocarbon products by passing, at elevated temperature and pressure, synthesis gas and a fluidising liquid through a fluidised catalytic bed within a reaction zone, characterised in that the fluidised catalytic bed is an aggregative fluidised catalytic bed comprising a particulate Fischer-Tropsch catalyst having a density of greater than 4,000 kg/m$^3$.

Advantages of employing an aggregative fluidised catalytic bed include:
1. The process being less constrained by the size of the catalyst particles and by the liquid fluidising velocity. In particular, an aggregative fluidised bed can be operated using a wide catalyst size distribution and/or with a liquid fluidising velocity above the terminal fall velocity, $U_t$, of the catalyst particles.
2. The presence of the "liquid bubbles" promote solid mixing within the fluidised bed.
3. The aggregative behaviour of the fluidised bed breaks up bubbles of synthesis gas thereby increasing both the mass transfer rate and the effective utilisation of the catalyst.
4. The process can be operated with a smaller catalytic bed than is employed in a conventional particulate fluidised bed process.

Suitably, the particulate Fischer-Tropsch catalyst is maintained in an aggregative fluidised state by the action of the flow of fluidising liquid through the reaction zone. Suitably, the rate of flow of fluidising liquid through the reaction zone is equal to or greater than the minimum fluidising velocity.

Suitably, the fluidising liquid comprises a hydrocarbon solvent. Preferably, the hydrocarbon solvent of the fluidising liquid may be one or more of the liquid hydrocarbon products which has an advantage that there is no requirement to separate the liquid hydrocarbon products from the hydrocarbon solvent. Preferably, the hydrocarbon solvent of the fluidising liquid is a high boiling hydrocarbon solvent. By high boiling hydrocarbon solvent is meant a hydrocarbon solvent having a boiling point, at standard pressure, of greater than 280° C.

Preferably, the liquid hydrocarbon products comprise a mixture of hydrocarbons having a chain length of greater than 5 carbon atoms. Suitably, the liquid hydrocarbon products comprise a mixture of hydrocarbons having chain lengths of from 5 to about 90 carbon atoms. Preferably, a major amount, for example, greater than 60% by weight, of the hydrocarbons have chain lengths of from 5 to 30 carbon atoms.

A low boiling solvent may also be introduced into the reaction zone. By low boiling solvent is meant a solvent having a boiling point, at standard pressure, in the range of from 30 to 280° C., preferably from 30 to 210° C. Preferably, the low boiling solvent is selected from the group consisting of aliphatic hydrocarbons having from 5 to 10 carbon atoms, alcohols (preferably, alcohols having from 1 to 4 carbon atoms, in particular, methanol), and water. In order to simplify the process, it is preferred that the low boiling solvent is a low boiling liquid hydrocarbon product or mixtures thereof. Without wishing to be bound by any theory, it is believed that vaporisation of the low boiling solvent in the reaction zone aids and enhances the mixing of the synthesis gas (hereinafter referred to as "syngas"), fluidising liquid and the particulate catalyst thereby increasing conversion of syngas to liquid hydrocarbon products. Moreover, vaporisation of the low boiling solvent will remove some of the exothermic heat of reaction thereby allowing more control over the product selectivities and minimising the production of gaseous by-products, for example, methane.

The aggregative fluidised bed may also be cooled within the reaction zone by means of a heat exchanger, for example, heat transfer tubes, positioned within the aggregative fluidised bed, to assist in removing exothermic heat of reaction from the system. A further advantage of an aggregative fluidised bed is that the presence of the "liquid bubbles" improves heat transfer to the heat transfer tubes.

In a first embodiment of the process of the present invention, a liquid stream containing entrained catalyst particles is withdrawn from the reaction zone and is passed to an external solid-liquid separator (for example, a filter, hydrocyclone or gravity separator) where the entrained catalyst particles are separated from the liquid stream thereby generating a substantially catalyst-free liquid stream (hereinafter "catalyst-free liquid stream"). Preferably, the separated catalyst particles are recycled from the external solid-liquid separator to the reaction zone as a concentrated slurry. The catalyst-free liquid stream is then passed from the external solid-liquid separator to a gas-liquid separator where a gaseous phase comprising unconverted syngas is separated from the catalyst-free liquid stream.

Without wishing to be bound by any theory, the liquid stream which is withdrawn from the reaction zone will contain entrained catalyst particles when (a) the liquid fluidizing velocity is substantially greater than the terminal fall velocity ($U_t$) of the largest catalyst particles in the bed and/or (b) the catalyst has a particle size distribution such that a proportion, preferably, a substantial proportion, of the catalyst particles have a $U_t$ below the liquid fluidizing velocity.

Alternatively, in a second embodiment of the process of the present invention, the reaction zone may be provided with an internal solid-liquid separator (for example, a filter, hydrocyclone or gravity separator). Suitably, the internal solid-liquid separator is positioned in the upper part of the reaction zone. Preferably, the internal solid-liquid separator is in communication with a catalyst-free zone. Catalyst particles are retained by the internal solid-liquid separator and catalyst-free liquid is passed, usually under pressure, from the internal solid-liquid separator to the catalyst-free zone. Preferably, the catalyst-free zone has a headspace above the level of the catalyst-free liquid. A gaseous phase comprising unconverted syngas separates from the catalyst-free liquid and accumulates in the headspace of the catalyst-free zone so that the catalyst-free zone acts as a gas-liquid separator. A gaseous stream comprising unconverted syngas is withdrawn from the headspace of the catalyst-free zone and a catalyst-free liquid stream is withdrawn from below the level of the catalyst-free liquid in the catalyst-free zone, for example, immediately after the solid-liquid separator. Suitably, the reaction zone and catalyst-free zone are zones within a Fischer-Tropsch reaction vessel.

Where the aggregative fluidised bed is partially expanded there is no requirement for a solid-liquid separator since catalyst-free liquid will be present in the reaction zone above the surface of the partially expanded bed. Expansion of an aggregative fluidised bed can be controlled by adjusting one or more of the following parameters: the liquid fluidising velocity, the rate of flow of gas through the aggregative fluidised bed, the catalyst particle size distribution and the density of the particulate catalyst.

Thus, in a third embodiment of the process of the present invention, a partially expanded aggregative fluidised bed (having catalyst-free liquid above the surface of the bed) is maintained in the reaction zone and a headspace is present in the reaction zone above the level of the catalyst-free liquid. A catalyst-free liquid stream is withdrawn from a region of the reaction zone which is above the surface of the partially expanded bed and below the level of the catalyst-free liquid. A gaseous phase comprising unconverted syngas separates from the catalyst-free liquid and accumulates in the headspace. Suitably, a gaseous stream comprising unconverted syngas is withdrawn from the headspace of the reaction zone.

Alternatively, in a fourth embodiment of the process of the present invention, a partially expanded aggregative fluidised bed (having catalyst-free liquid above the surface of the bed) is maintained in a reaction zone in the absence of a headspace. The reaction zone is in communication with a catalyst-free zone and catalyst-free liquid is passed, usually under pressure, from a region of the reaction zone which is above the surface of the partially expanded bed into the catalyst-free zone. Preferably, a headspace is present in the catalyst-free zone above the level of catalyst-free liquid. A gaseous phase comprising unconverted syngas separates from the catalyst-free liquid and accumulates in the headspace of the catalyst-free zone. Suitably, a gaseous stream comprising unconverted synthesis gas is withdrawn from the headspace and a catalyst-free liquid stream is withdrawn from below the level of catalyst-free liquid in the catalyst-free zone.

Preferably, at least a portion of the catalyst-free liquid stream (from the first, second or third embodiments of the present invention) is recycled to the reaction zone. Typically, the catalyst-free liquid stream is cooled, for example, by being passed through a heat exchanger, before being recycled to the reaction zone. It is envisaged that the catalyst-free liquid stream will contain residual gases/vapours (unconverted syngas, gaseous by-products, gaseous intermediate products, vaporised low boiling liquid hydrocarbon products, vaporised water by-product and any vaporised low boiling solvent) in which case low boiling liquid hydrocarbon products, water by-product and any low boiling solvent may condense in the heat exchanger. Residual gases may be separated from the catalyst-free liquid stream (and condensed liquid) in a gas-liquid separator, for example, a hydrocyclone. A gaseous stream from the gas-liquid separator may be recycled to the reaction zone and/or purged from the system. A liquid recycle stream is returned to the reaction zone (fluidising liquid) from the gas-liquid separator via a liquid pump. Suitably, a product side stream is taken from the liquid recycle stream downstream of the liquid pump and is passed to a product purification stage (described below). A further advantage of the process of the present invention is that fluidising liquid and not a suspension of particulate catalyst particles in the fluidising liquid is recycled to the reaction zone which reduces the duty on the liquid pump (size and power requirements).

Preferably, at least a portion of the gaseous stream comprising unconverted syngas which is withdrawn:
(i) from the headspace of the catalyst-free zone (second and fourth embodiments of the process of the present invention),
(ii) from the headspace of the reaction zone (third embodiment of the process of the present invention), or
(iii) from the external gas-liquid separator (first embodiment of the process of the present invention),
is recycled to the reaction zone (hereinafter referred to as "gaseous recycle stream").

The gaseous recycle stream additionally comprises gaseous intermediate hydrocarbon products (gaseous products having 2 or 3 carbon atoms, in particular, ethane or propanes), vaporised low boiling liquid hydrocarbon products (e.g. pentanes, hexanes or hexenes), vaporised water by-product, and any vaporised low boiling solvent.

The gaseous recycle stream is preferably cooled before being recycled to the reaction zone, for example, by passing the separated gaseous stream through a heat exchanger, to further assist in the removal of exothermic heat of reaction from the system. The gaseous recycle stream may be cooled to below its dew point to form a two phase mixture of gas (syngas, methane by-product, intermediate gaseous hydrocarbons) and condensed liquid (water by-product, low boiling liquid hydrocarbon products and any low boiling solvent). The condensed liquid may be recycled to the reaction zone entrained in the gaseous recycle stream. Alternatively, the condensed liquid may be separated from the gaseous recycle stream, for example, using a suitable gas-liquid separation means (e.g. a hydrocyclone, demister, gravity separator) and is recycled to the reaction zone, for example, using a nozzle. Preferably, excess water by-product is removed from the separated condensed liquids using a suitable separation means (e.g. a decanter), before recycling the condensed liquids to the reaction zone. It is envisaged that the heat exchanger and gas-liquid separation means may be combined within a single vessel in order to simplify recycling of the gaseous stream to the reaction zone.

Fresh syngas may be fed to the gaseous recycle stream, either upstream or downstream of the heat exchanger. Where the syngas has not been pre-cooled, it is preferred that the syngas is fed to the gaseous recycle stream upstream of the heat exchanger. Preferably, the gaseous recycle stream is recycled to the reaction zone via a blower or compressor located downstream of the heat exchanger. Suitably, the gaseous recycle stream is fed to the reaction zone via a gas sparger.

Preferably, a purge stream is taken from the gaseous recycle stream to prevent the accumulation of gaseous by-products, for example, methane, in the system. If desired, any gaseous intermediate products may be separated from the purge stream. Preferably, such gaseous intermediate products are recycled to the system where they may be converted to liquid hydrocarbon products. Preferably, the purge stream is taken downstream of the heat exchanger.

Preferably, the ratio of hydrogen to carbon monoxide of the syngas used in the process of the present invention is in the range of from 1:1 to 3:1 by volume, typically 2:1 by volume. Impurities such as methane, carbon dioxide, nitrogen and water may be present in the syngas.

The synthesis gas may be prepared using any of the processes known in the art including partial oxidation of hydrocarbons, steam reforming, and autothermal reforming. A discussion of these synthesis gas production technologies is provided in "Hydrocarbon Processing" V78, N.4, 87–90, 92–93 (April 1999) and "Petrole et Techniques", N. 415, 86–93 (July–August 1998). It is also envisaged that the synthesis gas may be obtained by catalytic partial oxidation of hydrocarbons in a microstructured reactor as exemplified in "IMRET 3: Proceedings of the Third International Conference on Microreaction Technology", Editor W Ehrfeld, Springer Verlag, 1999, pages 187–196. Alternatively, the synthesis gas may be obtained by short contact time catalytic partial oxidation of hydrocarbonaceous feedstocks as described in EP 0303438. Preferably, the synthesis gas is obtained via a "Compact Reformer" process as described in "Hydrocarbon Engineering", 2000, 5, (5), 67–69; "Hydrocarbon Processing", 79/9, 34 (September 2000); "Today's Refinery", 15/8, 9 (August 2000); WO 99/02254; and WO 200023689.

The catalyst which is employed in the process of the present invention may comprise any catalyst known to be active in Fischer-Tropsch synthesis which has a density of greater than 4,000 kg/m$^3$. For example, Group VIII metals whether supported or unsupported are known Fischer-Tropsch catalysts. Of these iron, cobalt and ruthenium are preferred, particularly iron and cobalt, most particularly cobalt.

A preferred catalyst is supported on a support Preferred supports include cobalt metal and iron metal. Suitably, the catalyst is coated onto the support. Typically, the coating is from sub-micron to several microns thickness.

The catalytic metal is present in catalytically active amounts in the coating usually about 1–100 wt %, the upper limit being attained in the case of iron based catalysts. Preferably, the amount of catalytic metal in the coating is about 2–40 wt %. Promoters may be added to the catalyst and are well known in the Fischer-Tropsch catalyst art. Promoters can include ruthenium (when it is not the primary catalyst metal), rhenium, hafnium, cerium, and zirconium, and are usually present in amounts less than the primary catalytic metal (except for ruthenium which may be present in coequal amounts), but the promoter:metal ratio should be at least 1:10. Preferred promoters are rhenium and hafnium.

A further advantage of the process of the present invention is that a wide size distribution of catalyst particle sizes can be employed compared with a conventional slurry process. Typically, the catalyst has a mean particle size in the range of from 20 to 1500 microns, preferably, 50 to 350 microns.

Suitably, the liquid recycle stream is introduced at or near the bottom of the reaction zone.

Suitably, gas (gaseous recycle stream and any fresh syngas) is sparged into the reaction zone through a sparger. Preferably, the sparger is positioned near the bottom of the reaction zone.

Preferably, the gas which is fed to the reaction zone comprises from 50 to 100% by volume of fresh syngas (make-up syngas).

Preferably, the aggregative fluidised bed has a diameter of less than 10 meters, for example, in the range of 0.5 to 8 meters and a height of less than 15 meters, for example, in the range of 1 to 10 meters.

The present invention can be operated in batch or continuous mode, the latter is preferred.

In a continuous process a product side stream is continuously removed from the liquid recycle stream and is passed to a product separation stage. In the product separation stage, liquid medium and liquid hydrocarbon products are separated from any fines (any catalyst particles which are carried over from the internal or external solid-liquid separator). The product separation stage comprises a suitable solid-liquid separation means. Examples of suitable liquid-solid separation means include hydrocyclones, filters, gravity separators and magnetic separators. Alternatively, the liquid medium and liquid hydrocarbon products may be separated from the fines by distillation. Preferably, there are two or more product side stream withdrawal lines leading to dedicated solid-liquid separation means. This ensures continuous operation of the process by allowing one or more of the solid-liquid separation means to be taken off-line for cleaning. The separated fines may be removed from the process or may be recycled from the solid-liquid separation means to the reaction zone. The separated liquid (liquid medium, liquid hydrocarbon products, any low boiling hydrocarbon solvent and any water by-product) is passed to a product purification stage. As discussed above, the purification stage may be simplified by using a liquid hydrocarbon product as the liquid medium which eliminates the requirement to separate the liquid medium from the liquid hydrocarbon products. In the purification stage, any water by-product is removed from the liquid hydrocarbon products.

In order to prevent the accumulation of water by-product in the system it is preferred that at least a portion of the water by-product is removed from the liquid recycle stream. This may be achieved by taking a side stream from the liquid recycle stream. Water by-product is removed from the side stream (for example, using a decanter) before returning the side stream to the reaction zone. It is envisaged that removal of water by-product from the system can be incorporated into the product purification stage, by recycling a portion of the separated liquids, from which water has been removed, back to the reaction zone.

The process of the invention is preferably carried out at a temperature of 180–280° C., more preferably 190–240° C.

The process of the invention is preferably carried out at a pressure of 5–50 bar, more preferably 15–35 bar, generally 20–30 bar.

The liquid hydrocarbon products from the product purification stage may be fed to a hydrocracking stage, for example, a catalytic hydrocracking stage which employs a catalyst comprising a metal selected from the group consisting of cobalt, molybdenum, nickel and tungsten supported on a support material such as alumina, silica-alumina or a zeolite. Preferably, the catalyst comprises cobalt/molybdenum or nickel/molybdenum supported on alumina or silica-alumina. Suitable hydrocracking catalysts include catalysts supplied by Akzo Nobel, Criterion, Chevron, or UOP.

BRIEF DESCRIPTION OF DRAWING

The invention will now be illustrated with the aid of a FIGURE.

Reactor vessel (1) comprises a reaction zone (2) and a catalyst-free zone (3). An aggregative fluidised catalytic bed (4) comprising a catalyst having a density of greater than 4,000 kg/m$^3$ fills the whole of the reaction zone (1). A headspace (5) is present in the catalyst-free zone (3) above the level (6) of catalyst-free fluidising liquid. The reaction zone (2) is maintained at a temperature of from 180 to 280° C. and at a pressure of from 5 to 50 bar. Cooling coils (7) are positioned within the aggregative fluidised bed to assist in removal of exothermic heat of reaction. Syngas is sparged into the reaction zone (2) via a sparger (8). An internal hydrocyclone (9) is positioned in the upper part of the reaction zone to separate catalyst particles from the fluidising liquid. Fluidising liquid is withdrawn after the internal hydrocyclone (9) via a line (10) and is passed through heat exchanger (11) which further assists in removing exothermic heat of reaction. The fluidising liquid is passed from the heat exchanger (11) to a gas-liquid separator (12) via line (13) where residual gas is separated from the fluidising liquid. A gaseous stream is withdrawn from the gas-liquid separator (12) via line (14). The gaseous stream may be recycled to the reaction zone and/or purged from the system (not shown). A liquid recycle stream, is also withdrawn from the gas-liquid separator (12) and is recycled to the reaction zone (2) via line (15), liquid pump (16) and line (17).

A product side stream (18) may be taken from the liquid recycle stream downstream of liquid pump (16) and is passed to product separation and purification stages (not shown).

A gaseous recycle stream comprising unconverted syngas, gaseous intermediate products, any vaporised low boiling solvent, any vaporised low boiling liquid hydrocarbon products and any vaporised water by-product may be withdrawn from the headspace (5) through line (19). By means of a heat exchanger (20), the gaseous recycle stream may be cooled to a temperature at which liquid condenses out. The condensed liquid (typically comprising low boiling hydrocarbon products, water by-product and any low boiling solvent) may be separated from the gaseous recycle stream in a gas-liquid separator (21). The condensed liquid may be withdrawn from the gas-liquid separator (21) via line (22) and may subsequently be recycled to the reaction zone (2), optionally after having removed water by-product (not shown). The gaseous recycle stream from the gas-liquid separator (21) is recycled to the reaction zone (2) via line (23), compressor/blower (24) and lines (25) and (26). A purge stream may be taken from the gaseous recycle stream via line (27) to prevent the build up of gaseous by-products (e.g. methane) in the reaction zone (2). Fresh syngas may be introduced to the sparger (8) via line (28).

We claim:

1. A process for the production of liquid hydrocarbon products by passing, at elevated temperature and pressure, synthesis gas and a fluidising liquid through a fluidised catalytic bed within a reaction zone, characterised in that the fluidised catalytic bed is an aggregative fluidised catalytic bed comprising a particulate Fischer-Tropsch catalyst having a density of greater than 4,000 kg/m$^3$.

2. A process as claimed in claim 1 wherein the liquid fluidising velocity is greater than the terminal fall velocity of the particulate Fischer-Tropsch catalyst and a liquid stream comprising fluidising liquid and liquid hydrocarbon products is withdrawn from the reaction zone together with entrained catalyst particles and is passed to an external solid-liquid separator wherein the entrained catalyst particles are separated from a catalyst free-liquid stream.

3. A process as claimed in claim 2 wherein the separated catalyst particles are recycled from the external solid-liquid separator to the reaction zone as a concentrated slurry.

4. A process as claimed in claim 2 wherein the catalyst-free liquid stream is passed to a gas-liquid separator wherein a gaseous stream comprising unconverted synthesis gas is separated from the catalyst-free liquid stream.

5. A process as claimed in claim 1 wherein the reaction zone is provided with an internal solid-liquid separator for separating catalyst-free liquid from the aggregative fluidised bed.

6. A process as claimed in claim 5 wherein the catalyst-free liquid is passed to a catalyst-free zone.

7. A process as claimed in claim 6 wherein the catalyst-free zone has a headspace above the level of the catalyst-free liquid and a gaseous phase comprising unconverted synthesis gas separates from the catalyst-free liquid and accumulates in the headspace.

8. A process as claimed in claim 7 wherein a gaseous stream comprising unconverted synthesis gas is withdrawn from the headspace of the catalyst free zone and a catalyst-free liquid stream comprising fluidising liquid and liquid hydrocarbon products is withdrawn from below the level of the catalyst free liquid in the catalyst free zone.

9. A process as claimed in claim 1 wherein a partially expanded aggregative fluidised bed is maintained within the reaction zone having a catalyst free-liquid region above the surface of the partially expanded bed.

10. A process as claimed in claim 9 wherein a headspace is present in the reaction zone above the level of the catalyst-free liquid and a gaseous phase comprising unconverted synthesis gas separates from the catalyst-free liquid and accumulates in the headspace.

11. A process as claimed in claim 10 wherein a catalyst-free liquid stream comprising fluidising liquid and liquid hydrocarbon products is withdrawn from a region of the reaction zone which is above the surface of the partially expanded bed and below the level of the catalyst free liquid and a gaseous stream comprising unconverted synthesis gas is withdrawn from the headspace of the reaction zone.

12. A process as claimed in claim 9 wherein the partially expanded aggregative fluidised bed is maintained in the reaction zone in the absence of a headspace.

13. A process as claimed in claim 12 wherein the reaction zone is in communication with a catalyst free zone and catalyst-free liquid is withdrawn from a region of the reaction zone which is above the surface of the partially expanded bed and is passed into the catalyst free zone.

14. A process as claimed in claim 13 wherein the catalyst free zone has a headspace above the level of the catalyst-free liquid and a gaseous phase comprising unconverted synthesis gas separates from the catalyst-free liquid and accumulates in the headspace.

15. A process as claimed in claim 14 wherein a gaseous stream comprising unconverted synthesis gas is withdrawn from the headspace of the catalyst-free zone and a catalyst-free liquid stream comprising fluidising liquid and liquid hydrocarbon products is withdrawn from below the level of the catalyst free liquid in the catalyst free zone.

16. A process as claimed in claim 1 wherein the fluidising liquid is a high boiling hydrocarbon solvent having a boiling point, at standard pressure, of greater than 280° C.

17. A process as claimed in claim 1 wherein a low boiling solvent having a boiling point, at standard pressure, in the range of from 30 to 280° C. is introduced into the reaction zone.

18. A process as claimed in claim 1 wherein the aggregative fluidised bed is cooled within the reaction zone by means of heat transfer tubes positioned within the aggregative fluidised bed.

19. A process as claimed in claim 4 wherein at least a portion of the gaseous stream comprising unconverted synthesis gas is recycled to the reaction zone.

20. A process as claimed in claim 19 wherein the gaseous stream is cooled before being recycled to the reaction zone.

21. A process as claimed in claim 2 wherein at least a portion of the catalyst-free liquid stream is recycled to the reaction zone.

22. A process as claimed in claim 21 wherein the catalyst-free liquid stream is cooled before being recycled to the reaction zone.

23. A process as claimed in claim 1 wherein the catalyst comprises iron or cobalt supported on a support.

24. A process as claimed in claim 23 wherein the support is cobalt metal or iron metal.

* * * * *